(12) United States Patent
Beamer et al.

(10) Patent No.: US 10,857,284 B2
(45) Date of Patent: Dec. 8, 2020

(54) INTRAOSSEOUS-NEEDLE STABILIZER AND METHODS

(71) Applicant: TELEFLEX LIFE SCIENCES LIMITED, Valletta (MT)

(72) Inventors: Cynthia L. Beamer, Helotes, TX (US); Chris Kilcoin, South Lake Tahoe, CA (US)

(73) Assignee: TELEFLEX LIFE SCIENCES LIMITED, Vallette (MT)

( * ) Notice: Subject to any disclaimer, the term of this patent is extended or adjusted under 35 U.S.C. 154(b) by 0 days.

(21) Appl. No.: 15/824,042

(22) Filed: Nov. 28, 2017

(65) Prior Publication Data

US 2018/0078702 A1    Mar. 22, 2018

Related U.S. Application Data

(63) Continuation of application No. 13/576,943, filed as application No. PCT/US2011/023496 on Feb. 2, 2011, now Pat. No. 9,839,740.

(60) Provisional application No. 61/184,035, filed on Feb. 2, 2010.

(51) Int. Cl.
| | | |
|---|---|---|
| A61M 5/00 | (2006.01) | |
| A61B 17/34 | (2006.01) | |
| A61M 5/158 | (2006.01) | |

(52) U.S. Cl.
CPC ........... *A61M 5/00* (2013.01); *A61B 17/3472* (2013.01); *A61M 5/158* (2013.01); *A61B 2017/3492* (2013.01); *A61M 2005/1585* (2013.01); *A61M 2210/02* (2013.01)

(58) Field of Classification Search
CPC .................... A61M 5/00; A61M 5/158; A61M 2005/1581; A61M 2005/1585; A61M 2005/1586; A61M 2210/02; A61M 2202/10; A61B 17/3472; A61B 2017/3492
See application file for complete search history.

(56) References Cited

U.S. PATENT DOCUMENTS

| | | |
|---|---|---|
| 2,001,638 A | 5/1935 | Tornsjo |
| 2,317,648 A | 4/1943 | Siqveland |
| 3,815,605 A | 6/1974 | Schmidt et al. |
| 3,991,765 A | 11/1976 | Cohen |
| 4,142,517 A | 3/1979 | Stavropoulos |
| 4,170,993 A | 10/1979 | Alvarez |

(Continued)

FOREIGN PATENT DOCUMENTS

| | | |
|---|---|---|
| CA | 2138842 | 6/1996 |
| CA | 2454600 | 2/2003 |

(Continued)

OTHER PUBLICATIONS

"Proven reliability for quality bone marrow samples", Special Procedures, Cardinal Health, 6 pages, 2003.

(Continued)

*Primary Examiner* — Kami A Bosworth
*Assistant Examiner* — Leah J Swanson
(74) *Attorney, Agent, or Firm* — BakerHostetler

(57) ABSTRACT

Stabilizers for intraosseous devices, such as, for example, stabilizers that may be coupled to an intraosseous device (e.g., a device including an intraosseous needle) while a portion of the device extends into a patient's bone and/or while the device is coupled to a fluid source (e.g., FV bag, syringe, etc.).

21 Claims, 4 Drawing Sheets

(56) References Cited

U.S. PATENT DOCUMENTS

| | | | |
|---|---|---|---|
| 4,646,731 A | 3/1987 | Brower | |
| 4,659,329 A | 4/1987 | Annis | |
| 4,699,616 A * | 10/1987 | Nowak | A61M 25/02 |
| | | | 128/DIG. 26 |
| 4,758,225 A | 7/1988 | Cox et al. | |
| 4,772,261 A | 9/1988 | Von Hoff et al. | |
| 4,969,870 A | 11/1990 | Kramer et al. | |
| 5,057,085 A | 10/1991 | Kopans | |
| 5,116,324 A | 5/1992 | Brierley et al. | |
| 5,120,312 A | 6/1992 | Wigness et al. | |
| 5,122,114 A | 6/1992 | Miller et al. | |
| 5,195,985 A | 3/1993 | Hall | |
| 5,203,056 A | 4/1993 | Funk et al. | |
| 5,312,364 A | 5/1994 | Jacobs | |
| 5,332,398 A | 7/1994 | Miller et al. | |
| 5,372,583 A | 12/1994 | Roberts et al. | |
| 5,385,553 A | 1/1995 | Hart et al. | |
| 5,423,824 A | 6/1995 | Akerfeldt et al. | |
| 5,431,655 A | 7/1995 | Melker et al. | |
| 5,451,210 A | 9/1995 | Kramer et al. | |
| 5,484,442 A | 1/1996 | Melker et al. | |
| 5,591,188 A | 1/1997 | Waisman | |
| 5,601,559 A | 2/1997 | Melker et al. | |
| 5,733,262 A | 3/1998 | Paul | |
| 5,769,086 A | 6/1998 | Ritchart et al. | |
| 5,779,708 A | 7/1998 | Wu | |
| 5,858,005 A | 1/1999 | Krisel | |
| 5,868,711 A | 2/1999 | Kramer et al. | |
| 5,960,797 A | 10/1999 | Kramer et al. | |
| 6,018,094 A | 1/2000 | Fox | |
| 6,228,088 B1 | 5/2001 | Miller et al. | |
| 7,008,383 B1 | 3/2006 | Damadian et al. | |
| 7,137,985 B2 | 11/2006 | Jahng | |
| 7,207,949 B2 | 4/2007 | Miles | |
| 7,615,043 B2 | 11/2009 | Zhou | |
| 7,670,328 B2 | 3/2010 | Miller | |
| 7,699,850 B2 | 4/2010 | Miller | |
| 7,811,260 B2 | 10/2010 | Miller et al. | |
| 7,815,642 B2 | 10/2010 | Miller | |
| 7,850,620 B2 | 12/2010 | Miller et al. | |
| 7,899,528 B2 | 3/2011 | Miller et al. | |
| 7,951,089 B2 | 5/2011 | Miller | |
| 8,038,664 B2 | 10/2011 | Miller et al. | |
| 8,217,561 B2 | 7/2012 | Fukuzawa | |
| 8,308,693 B2 | 11/2012 | Miller et al. | |
| 8,419,683 B2 | 4/2013 | Miller et al. | |
| 8,480,632 B2 | 7/2013 | Miller et al. | |
| 8,506,568 B2 | 8/2013 | Miller | |
| 8,641,715 B2 | 2/2014 | Miller | |
| 8,656,929 B2 | 2/2014 | Miller et al. | |
| 8,668,698 B2 | 3/2014 | Miller et al. | |
| 8,684,978 B2 | 4/2014 | Miller et al. | |
| 8,690,791 B2 | 4/2014 | Miller | |
| 8,715,287 B2 | 5/2014 | Miller | |
| 8,812,101 B2 | 8/2014 | Miller et al. | |
| 2003/0225344 A1 | 12/2003 | Miller | |
| 2003/0225411 A1 | 12/2003 | Miller | |
| 2004/0064136 A1 | 4/2004 | Papineau et al. | |
| 2004/0220497 A1 | 11/2004 | Findlay et al. | |
| 2005/0027210 A1 | 2/2005 | Miller | |
| 2005/0038453 A1 | 2/2005 | Raulerson | |
| 2005/0040060 A1 | 2/2005 | Andersen et al. | |
| 2005/0131345 A1 | 6/2005 | Miller | |
| 2005/0148940 A1 | 7/2005 | Miller | |
| 2005/0165403 A1 | 7/2005 | Miller | |
| 2005/0165404 A1 | 7/2005 | Miller | |
| 2005/0171504 A1 | 8/2005 | Miller | |
| 2005/0182420 A1 | 8/2005 | Schulte et al. | |
| 2005/0228309 A1 | 10/2005 | Fisher et al. | |
| 2005/0261693 A1 | 11/2005 | Miller et al. | |
| 2006/0030825 A1 | 2/2006 | Enns | |
| 2006/0036212 A1 | 2/2006 | Miller | |
| 2006/0052790 A1 | 3/2006 | Miller | |
| 2006/0167378 A1 | 7/2006 | Miller | |
| 2006/0167379 A1 | 7/2006 | Miller | |
| 2006/0184063 A1 | 8/2006 | Miller | |
| 2006/0247577 A1 | 11/2006 | Wright | |
| 2007/0016100 A1 | 1/2007 | Miller | |
| 2007/0049945 A1 | 3/2007 | Miller | |
| 2007/0149920 A1 | 6/2007 | Michels et al. | |
| 2008/0045861 A1 | 2/2008 | Miller et al. | |
| 2008/0045965 A1 | 2/2008 | Miller et al. | |
| 2008/0140014 A1 | 6/2008 | Miller et al. | |
| 2008/0215056 A1 | 9/2008 | Miller et al. | |
| 2008/0221580 A1 | 9/2008 | Miller et al. | |
| 2010/0004626 A1 | 1/2010 | Miller et al. | |
| 2010/0010449 A1 * | 1/2010 | Leibowitz | A61B 17/3421 |
| | | | 604/179 |

FOREIGN PATENT DOCUMENTS

| | | |
|---|---|---|
| EP | 0984809 | 3/2000 |
| FR | 2457105 | 12/1980 |
| WO | 02/096497 | 12/2002 |
| WO | 2005/112800 | 12/2005 |
| WO | 2008/081438 | 7/2008 |

OTHER PUBLICATIONS

"Vidacare Comments on Infusion Nurses Society Position Paper on Intraosseous Vascular Access," May 4, 2009.

Astrom, K. Gunnar O., "CT-guided Transsternal Core Biopsy of Anterior Mediastinal Masses," Radiology 1996; 199:564-567.

Astrom, K.G., "Automatic Biopsy Instruments Used Through a Coaxial Bone Biopsy System with an Eccentric Drill Tip," Acta Radiologica, 1995; 36:237-242.

BioAccess.com, Single Use Small Bone Power Tool—How It Works, 1 pg. Jun. 9, 2008.

Buckley et al., CT-guided bone biopsy: Initial experience with commercially available hand held Black and Decker drill, European Journal of Radiology 61, pp. 176-180, 2007.

Cummins, Richard O., et al, "Acls-Principles and Practice", ACLS—The Reference Textbook, American Heart Association, pp. 214-218, 2003.

F.A.S.T. I Intraosseous Infusion System with Depth-Control Mechanism Brochure, 6 pages, 2000.

Gunal et al., Compartment Syndrome After Intraosseous Infusion: An Expiremental Study in Dogs, Journal of Pediatric Surgery. 31 (11):1491-1493, 1996.

Hakan et al., CT-guided Bone BiopsyPerformed by Means of Coaxial Bopsy System with an Eccentric Drill, Radiology, pp. 549-552, 1993.

International Preliminary Report on Patentability in PCT Application No. PCT/US2011/023496, dated Aug. 16, 2012.

International Search Report and Written Opinion issued in PCT Application No. PCT/US2011/023496, dated Oct. 24, 2011.

International Search Report and Written Opinion issued in PCT Application No. PCT/US2007/072217 dated Mar. 31, 2008.

International Search Report and Written Opinion issued in PCT Application No. PCT/US2007/072209 dated Apr. 25, 2008.

Liakat A. Parapia, Trepanning or trephines: a history of bone marrow biopsy, British Journal of Haematology, pp. 14-19, 2007.

Michael Trotty, "Technology (A Special Report)—The Wall Street Journal2008 Technology Innovation Awards—This years winners include: an IV alternative, a better way to make solar panels, a cheap, fuel efficient car and a better way to see in the dark", The Wall Street Journal, Factiva, 5 pages, 2008.

Office Communication in European Application No. 03756317.8 dated Dec. 28, 2006.

Office Communication issued in Chinese Patent Application No. 200780000585.5, dated Feb. 29, 2012.

Office Communication issued in Chinese Patent Application No. 200780000585.5, dated Nov. 19, 2010.

Office Communication issued in Taiwanese Patent Application No. 096140082, dated Mar. 27, 2013.

Pediatrics, Official Journal of the American Academy of Pediatrics, Pediatrics, 2005 American Heart Association Guidelines for Cardiopulmonary Resuscitation and Emergency Cardiovascular Care of

(56) References Cited

OTHER PUBLICATIONS

Pediatric and Neonatal Patients:Pediatric Advanced Life Support, Downloaded from www .pediatrics.org, Feb. 21, 2007.
Riley et al., "A Pathologist's Perspective on Bone Marrow Aspiration Biopsy: I. Performing a Bone Marrow Examination," Journal of Clinical Laboratory Analysis 18, pp. 70-90, 2004.

* cited by examiner

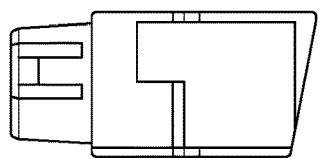
FIG. 8E
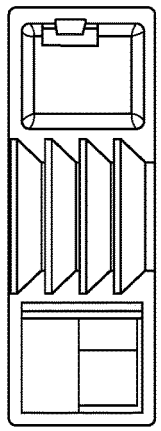
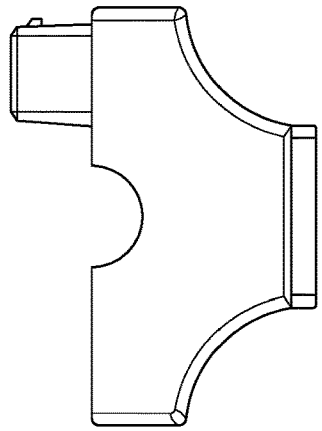
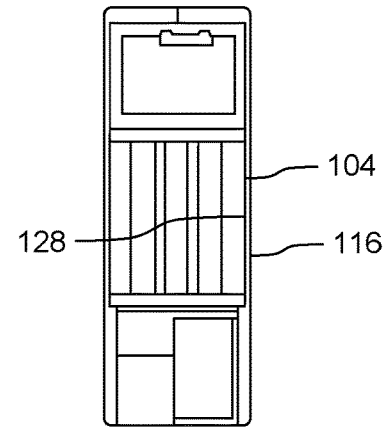
FIG. 8B  FIG. 8A  FIG. 8C
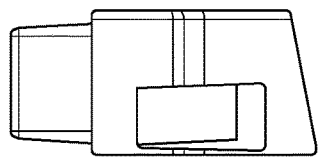
FIG. 8D
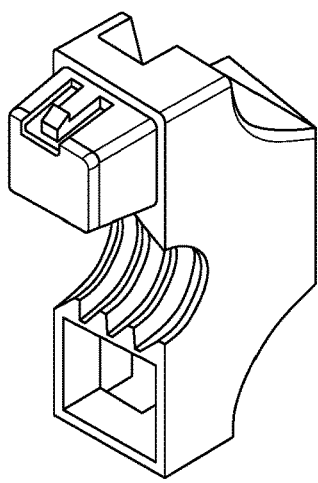
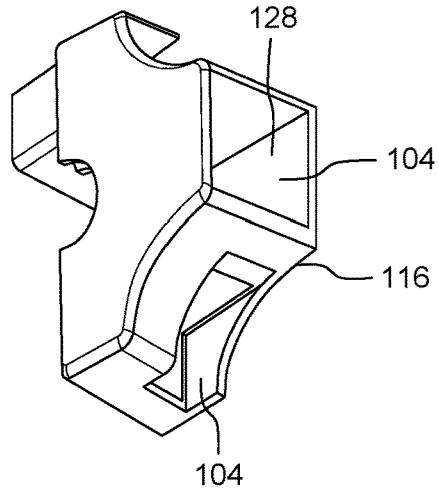
FIG. 8F  FIG. 8G

INTRAOSSEOUS-NEEDLE STABILIZER AND METHODS

CROSS-REFERENCE TO RELATED APPLICATION

This application is a continuation of U.S. patent application Ser. No. 13/576,943, filed Dec. 24, 2012, which is a national phase application under 35 U.S.C. § 371 of International Application No. PCT/US2011/023496, filed Feb. 2, 2011, which claims priority to U.S. Provisional Patent Application No. 61/184,035, filed Feb. 2, 2010. The entire text of each of the above-referenced applications is incorporated by reference herein in their entirety.

BACKGROUND

1. Field of the Invention

The present invention relates generally to accessing intraosseous blood vessels and, more particularly, but not by way of limitation, to stabilizers for intraosseous devices.

2. Description of Related Art

Intraosseous devices and support devices are known in the art. One example of an intraosseous device (including a needle) and support device is disclosed in U.S. patent application Ser. No. 11/619,390, filed Jan. 3, 2007, and published as Patent Pub. No. US 2008/0140014; which is incorporated by reference in its entirety.

SUMMARY

Some embodiments of the present apparatuses comprise: two members configured to be coupled together such that the members cooperate to encircle an intraosseous device to resist movement of the intraosseous device relative to the members; and one or more flexible tabs each coupled to at least one of the members and comprising an adhesive layer configured to be coupled to skin of a patient. In some embodiments, the apparatus is non-sterile. In some embodiments, the two members are substantially identical.

In some embodiments, the two members each comprise two connection portions. In some embodiments, the two connection portions comprise a male connection portion and a female connection portion. In some embodiments, the male connection portion comprises a resilient barb, and the female connection portion comprises a ledge configured such that if the members are coupled together, the resilient barb of each member contacts the ledge of the other member to resist separation of the members.

In some embodiments, the two members each comprise a coupling surface between the two connection portions, the coupling surface configured such that if the two members are coupled together, the coupling surfaces cooperate to define a device opening in which a portion of an intraosseous device can be positioned. In some embodiments, the members each have a proximal surface configured to face the patient's skin, and if the members are coupled together a longitudinal axis of the device opening is disposed at a non-zero angle relative to a plane of the proximal surface. In some embodiments, the longitudinal axis of the device opening is substantially perpendicular to a plane of the proximal surface. In some embodiments, the coupling surface of each member defines a groove configured to receive a flange of an intraosseous device. In some embodiments, the coupling surface of each member defines a plurality of grooves each configured to receive a flange of an intraosseous device in a different position of the intraosseous device relative to the proximal surface of the member. In some embodiments, the plurality of grooves in the coupling surface are each shaped to correspond to a portion of an intraosseous device.

In some embodiments, each member comprises a lower sidewall, and one of the one or more flexible tabs is coupled to the lower sidewall. In some embodiments, the one or more flexible tabs each comprises: a double-sided tape layer having an upper side coupled to a lower surface of the lower sidewall; and a single-sided tape layer having an adhesive side coupled to an upper surface of the lower sidewall and to a portion of the upper side of the double-sided tape layer that is not coupled to the lower surface of the lower sidewall. In some embodiments, the one or more flexible tabs each comprises: a liner layer coupled to a lower side of the double-sided tape layer; where the liner layer is configured to be removable from the lower side of the double-sided tape layer such that the lower side of the double-sided tape layer can be coupled to skin of a patient. In some embodiments, the liner layer extends beyond at least one peripheral edge of the double-sided tape layer. In some embodiments, when the members are coupled together around the hub of an intraosseous device, and the tabs are coupled to skin, the apparatus may keep the intraosseous device to which it has been coupled (and, particularly, the hub of the device and any fitting and associated tubing connected to it) in a stable position relative to the patient by, for example, resisting movement of the device and any associated connector relative to the patient.

In some embodiments, at least one lateral dimension of at least one of the flexible tabs, when flattened, does not exceed 4 inches. In some embodiments, at least one lateral dimension of at least one of the flexible tabs, when flattened, does not exceed 3.1 inches. In some embodiments, if the members are coupled together, the members fit within a rectangular volume no greater than 6 inches cubed. In some embodiments, if the members are coupled together, the members fit within a rectangular volume no greater than 4 inches cubed.

Some embodiments of the present kits comprise: three or more members each configured to be coupled to any of the other plurality of members such that the coupled members cooperate to encircle an intraosseous device to resist movement of the intraosseous device relative to the members; and a plurality of flexible tabs each coupled to at least one of the members and comprising an adhesive layer configured to be coupled to skin of a patient. In some embodiments, at least one of the three or members comprises one or more of the features of a member of the present apparatuses.

Some embodiments of the present components comprise: a member; and a flexible tab coupled to the member and comprising an adhesive layer configured to be coupled to skin of a patient; where the member is configured to be coupled a substantially identical member such that the coupled members cooperate to encircle an intraosseous device to resist movement of the intraosseous device relative to the members. In some embodiments, the apparatus is non-sterile. the member comprises one or more features of a member of the present apparatuses.

Some embodiments of the present methods comprise: coupling any embodiment of the present apparatuses to an intraosseous device having a portion extending into a bone of a patient; and coupling the adhesive layer of at least one of the one or more flexible tabs to the patient such that the apparatus resists motion of the members relative to the skin to which the adhesive layer is coupled. In some embodiments, the apparatus is non-sterile. In some embodiments, coupling the apparatus to the intraosseous device is performed while the intraosseous device is coupled to a fluid source.

Some embodiments of the present apparatuses comprise: coupling a support apparatus to an intraosseous device having a portion extending into a bone of patient while the intraosseous device is coupled to a fluid source; and coupling the support apparatus to the skin of patient such that the support apparatus resists displacement of the intraosseous device relative to the skin to which the support apparatus is coupled.

In any embodiment of the present disclosure, the term "substantially" may be substituted with "within [a percentage] of" what is specified, where the percentage includes 5, 10, and/or 15 percent.

Any embodiment of any of the present devices and kits can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIGS. 8A-8G depicts various views of the member of FIG. 6.

DESCRIPTION OF ILLUSTRATIVE EMBODIMENTS

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art.

The terms "comprise" (and any form of comprise, e.g., "comprises" and "comprising"), "have" (and any form of have, e.g., "has" and "having"), "include" (and any form of include, e.g., "includes" and "including") and "contain" (and any form of contain, e.g., "contains" and "containing") are open-ended linking verbs. As a result, a device or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a device or structure that is configured in a certain way is configured in at least that way, but it can also be configured in other ways than those specifically described. As used in this disclosure, a part or component that is unitary with another part or component means that the parts are of a physically continuous piece of material (e.g., are not physically separate from one another). For example, two of the present members may be of unitary construction if molded or otherwise formed as a single piece of material (e.g., with a flexible piece of material joining the two members in such a way that their connection portions may fixedly couple the two members together, as described in more detail below, and that also maintains a flexible connection between the two members if their connection portions are not coupled together).

Some embodiments of the present stabilizers are configured to couple an intraosseous (sometimes referred to as an interosseous) device to various bones and/or through various sites on a patient (e.g., arm, leg, sternum, shoulder. Examples of such intraosseous devices include the EZ-IO line of products offered by Vidacare Corporation, San Antonio, Tex., USA; and may include a hub with a cannula and/or an intraosseous needle (the intraosseous needle may be removable after insertion of the device such that a portion of the device extends into a bone of a patent).

Figure 1:
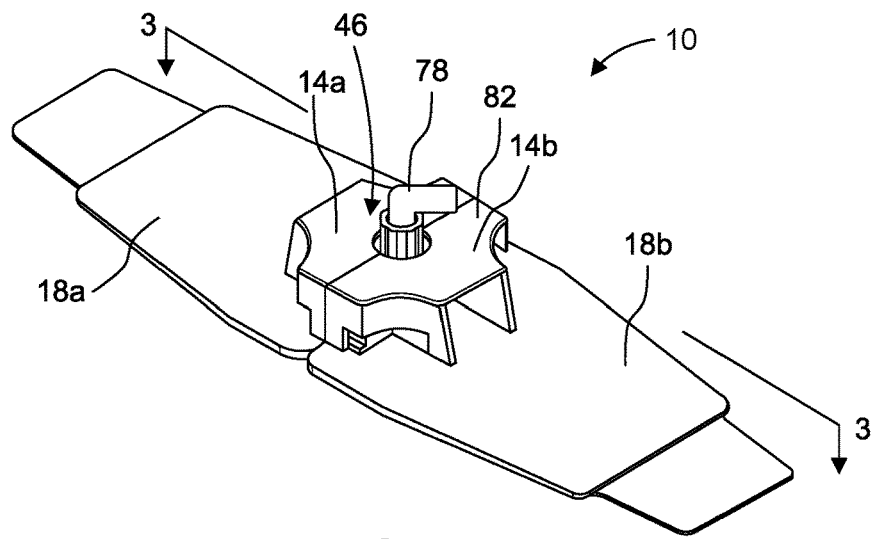
FIG. 1 depicts a perspective view of one embodiment of the present stabilizers which includes two stabilizer members and two flexible tabs.
Figure 2:
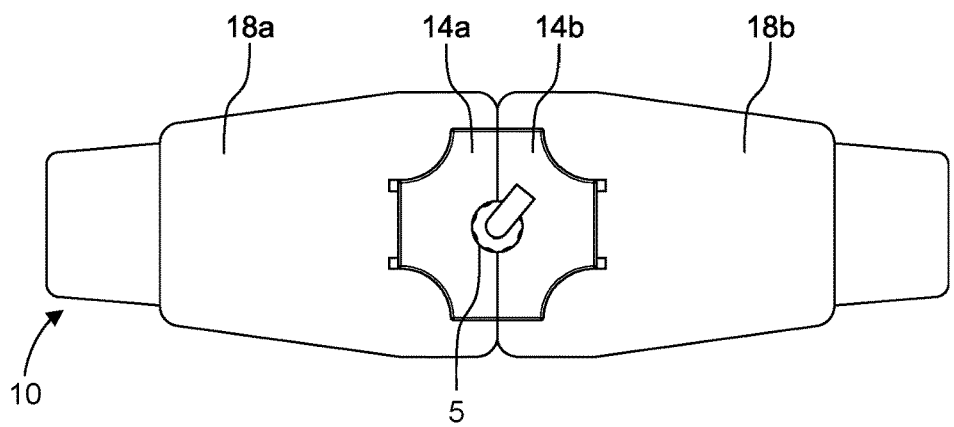
FIG. 2 depicts a top view of the stabilizer of FIG. 1.
Figure 3:
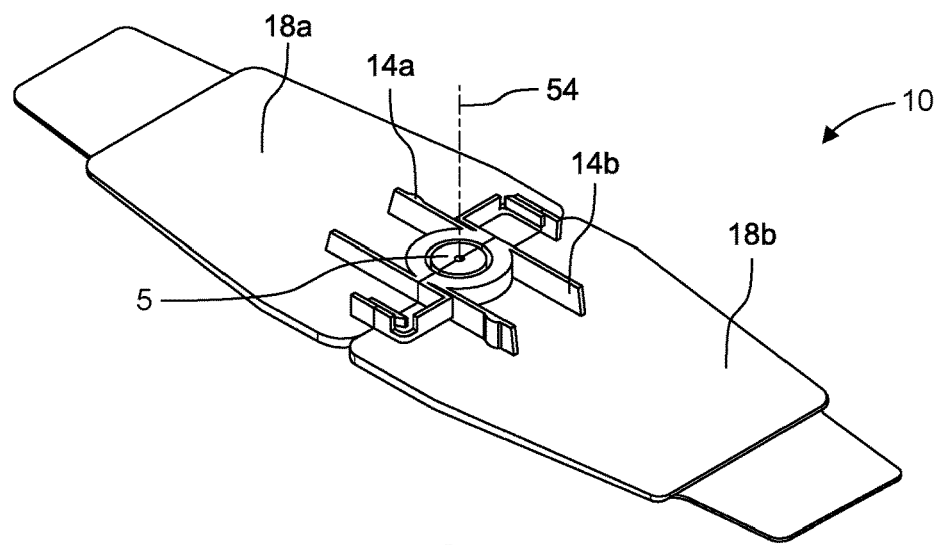
FIG. 3 depicts a perspective cross-sectional view of the stabilizer of FIG. 1 taken along the line 3-3 of FIG. 1.
Figure 4:
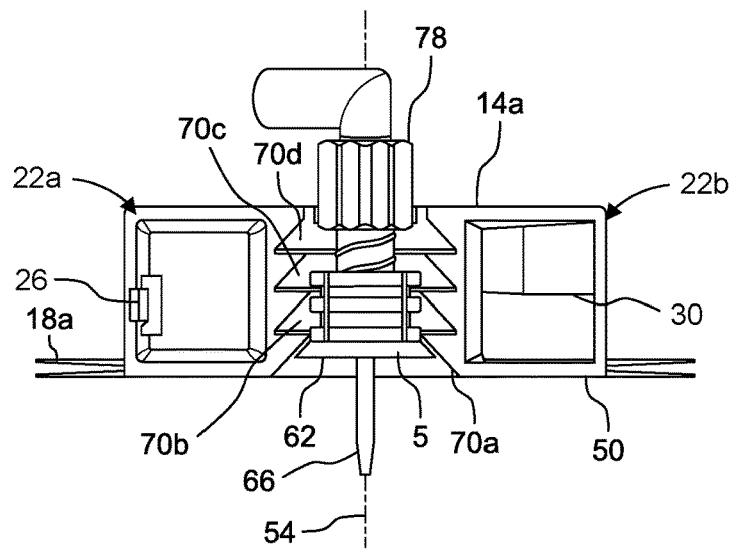
FIG. 4 depicts a side view of a member of the stabilizer of FIG. 1 shown with an intraosseous device in a first position relative to the stabilizer.
Figure 5:
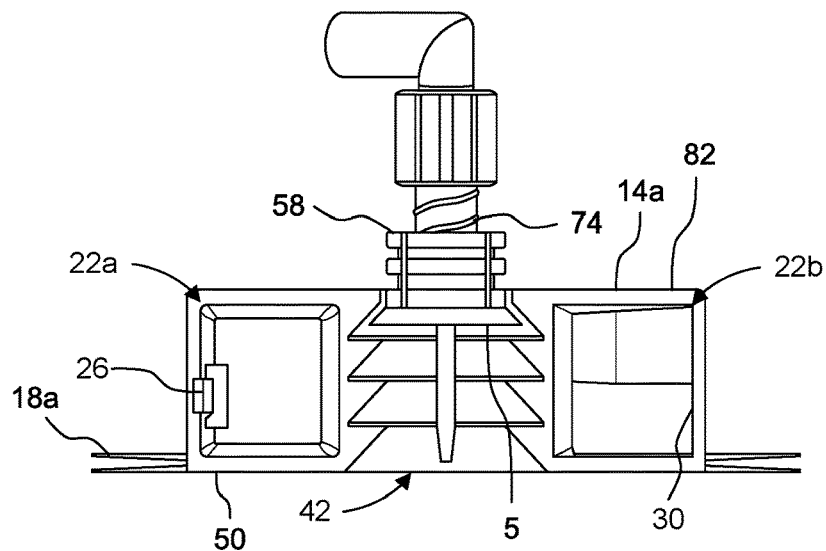
FIG. 5 depicts a side view of a member of the stabilizer of FIG. 1 shown with an intraosseous device in a second position relative to the stabilizer.

Referring now to the drawings, and more particularly to FIGS. 1-5, shown therein and designated by the reference numeral 10 is an embodiment of the present stabilizers. FIG. 1 depicts a perspective view of stabilizers 10 that includes two stabilizer members 14a, 14b, and two flexible tabs 18a, 18b. FIG. 2 depicts a top view of stabilizer 10. FIG. 3 depicts a perspective cross-sectional view of stabilizer 10 taken along the line 3-3 of FIG. 1. FIG. 4 depicts a side view of member 14a of stabilizer 10 shown with an intraosseous device 5 in a first position relative to the stabilizer. FIG. 5 depicts a side view of member 14a of stabilizer 10 shown with intraosseous device 5 in a second position relative to the stabilizer.

In the embodiment shown, members 14a and 14b are configured to be coupled together (and are shown coupled together) such that members 14a and 14b cooperate to encircle intraosseous device 5 (e.g., such that neither member individually encircles device 5) to resist movement of intraosseous device 5 relative to members 14a and 14b. In some embodiments, stabilizer 10 comprises one or more flexible tabs (18a, 18b) each coupled to at least one of the members (14a, 14b) and comprising an adhesive layer (not shown) configured to be coupled to skin of a patient. For example, in the embodiment shown, stabilizer 10 comprises two flexible tabs 18a and 18b each coupled to a different one of members 14a and 14b, respectively. Once the flexible tabs have been coupled to skin, the stabilizer is designed to keep the intraosseous device to which it has been coupled (and, particularly, the hub of the device and any fitting and associated tubing connected to it) in a stable position relative to the patient, which may entail resisting movement of the device and any associated connector relative to the patient.

In some embodiments, members 14a, 14b are resilient and/or at least partially rigid. For example, members 14a, 14b may each have a portion (e.g., a portion configured to contact device 5) that is substantially rigid, and another portion configured to resiliently flex (e.g., be deflectable to be coupled to the other members, as described in more detail below). Members 14a and 14b may comprise any suitable material, such as, for example, plastic(s), metal(s), alloy(s), composite(s), or the like, that permits the members to function as described in this disclosure. In other embodiments, members 14a and 14b may have any suitable outer shape, such as, for example, arcuate, curved, square, and/or may be expanded or indented in some portions to improve a user's ability to grip the member and/or the stabilizer.

Figure 6:
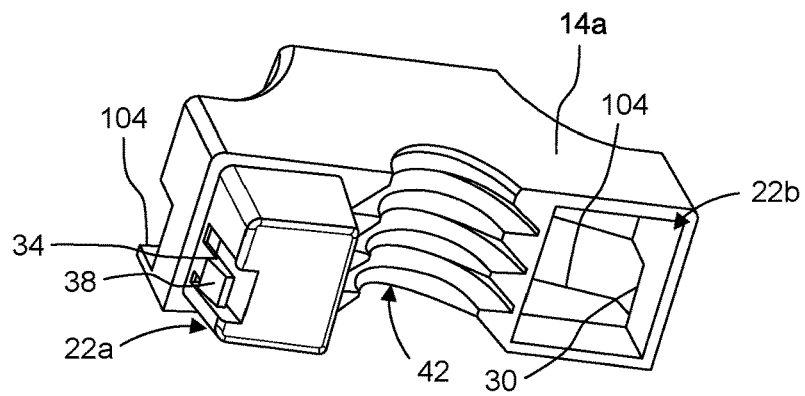
FIG. 6 depicts a perspective view of a member of the stabilizer of FIG. 1.

In the embodiment shown, members 14a and 14b are substantially identical. As such, only a single member 14a is shown in each of FIGS. 4 and 5. FIG. 6 depicts a perspective view of member 14a without tab 18a. In other embodiments, members 14a and 14b may differ (e.g., may have different connection portions, shapes, and/or the like). In the embodiment shown, member 14a comprises two connection portions 22a and 22b. In the embodiment shown, connection portion 22a is configured as a male connection portion, and connection portion 22b is configured as a female connection portion. Stated another way, in the embodiment shown, male connection portion 22a is configured to be inserted into a corresponding female connection portion 22b of another member (e.g., 14b), and female connection portion 22b is configured to receive a corresponding male connection portion 22a of another member (e.g., 14b).

In the embodiment shown, male connection portion 22a comprises a resilient barb 26, and the female connection portion comprises a ledge 30 configured such that if members 14a and 14b are coupled together (e.g., with male connection portion 22a of member 14a extending female connection portion 22b of member 14b, and with male connection portion 22a of member 14b extending into female connection portion 22b of member 14a), the resilient barb (26) of each member (14a or 14b) contacts the ledge (30) of the other member (14b or 14a) to resist separation of the members (14a and 14b). In the embodiment shown, barb 26 comprises an arm 34 configured to flex (be deflectable) relative to the rest of member 14a, and a projection 38 (e.g., a tapered projection), such that as members 14a and 14b are pressed together to be coupled, arm 34 of member 14a flexes inward (toward female connection member 22b of member 14a) until projection 38 moves past ledge 30 of member 14b, at which point arm 34 flexes outward such that projection 38 extends past ledge 30 and thereby mechanically resists separation of members 14a and 14b. In other embodiments, connection portions 22a and 22b can have any functional configuration, such as, for example: both connection portions 22a and 22b of member 14a may be configured as male connection portions, and both connection portions 22a and 22b of member 14b may be configured as female connection portions; each of connection portions 22a and 22b may comprise a male component and a female component; each of connection portions 22a and 22b can comprise a serrated or saw-tooth configuration; and/or the like.

In the embodiment shown, member 14a comprises a coupling surface 42 between connection portions 22a and 22b, and coupling surface 42 is configured such that if the two members are coupled together, the coupling surfaces cooperate to define a device opening 46 in which a portion of an intraosseous device can be positioned (e.g., as shown in FIGS. 1-3). In the embodiment shown, member 14a has a proximal surface 50 (e.g., at or near the plane of tab 18a shown in FIGS. 5-6) configured to face the patient's skin. In the embodiment shown, members 14a and 14b are configured such that if members 14a and 14b are coupled together a longitudinal axis 54 of device opening 46 is disposed at a non-zero angle (e.g., 90 degrees) relative to a plane of proximal surface 50.

In the embodiment shown, device 5 comprises a hub 58, a flange 62, and a cannula 66 (e.g., a needle may extend through cannula 66 during insertion of cannula into a patient's bone). In some embodiments, coupling surface 42 defines at least one groove 70 configured to receive a flange (e.g., 62) of an intraosseous device. For example, in the embodiment shown, coupling surface 42 defines a plurality of grooves 70a, 70b, 70c, 70d each configured to receive a flange (e.g., 62) of an intraosseous device in a different position of the intraosseous device relative to proximal surface 50 of the member (e.g., if flange 62 is received in groove 70a then flange may be adjacent the patient's skin (or the position the patient's skin would be absent an injury); and if flange 62 is received in any of grooves 70b, 70c, 70d then flange 62 may be spaced apart from a patient's skin at a position predetermined by the position of the groove in which the flange is received. In the embodiment shown, grooves 70a, 70b, 70c, 70d are shaped to correspond to a portion of an intraosseous device (e.g., as shown, grooves 70a, 70b, 70c, 70d are tapered between a relatively larger proximal end closest proximal surface 50 and a relatively smaller distal end that is farther from proximal surface 50).

As shown, intraosseous device 5 may comprise a fitting 74 (e.g., a Luer lock fitting, or the like) to which a fluid source 78 (a structure from or through which fluid may be delivered to device 5, such as, for example, a tube couplable to an IV bag, and IV bag, a syringe, and/or the like). In the embodiment shown, member 14 has a height or thickness between proximal surface 50 and a distal surface 82 that permits fitting 74 to extend above distal surface 82 to be accessible while stabilizer 10 is coupled to device 5 and/or permits stabilizer 10 to be coupled to device 5 while a fluid source 78 is coupled to device 5. In some embodiments, stabilizer 10 is non-sterile (is not sterile).

Figure 7A:
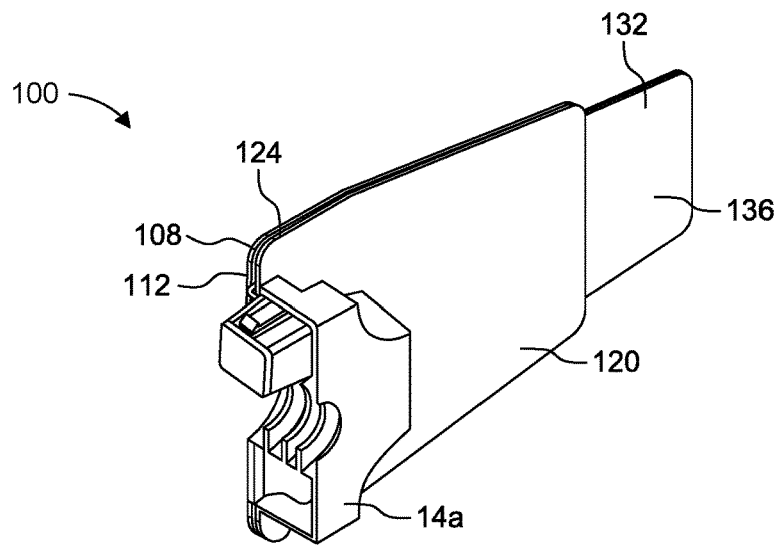
FIGS. 7A-7C depicts various views of a member and a flexible tab of the stabilizer of FIG. 1.
Figure 7B:
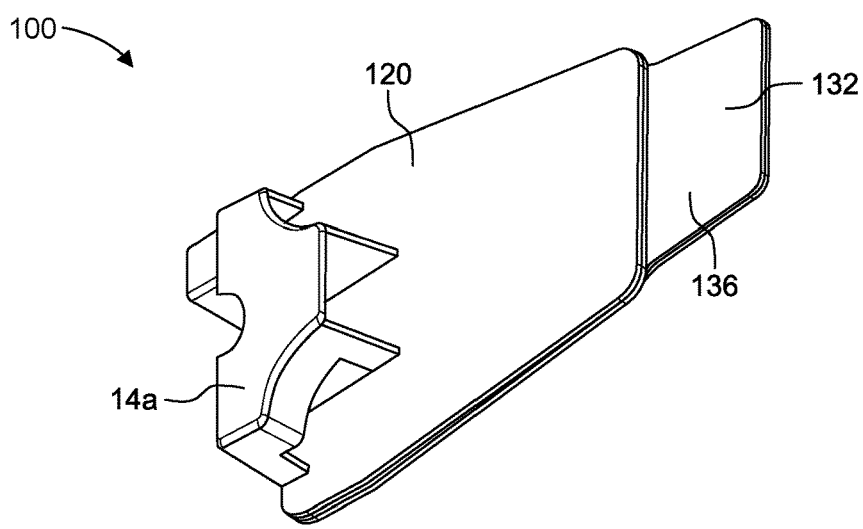
Figure 7C:
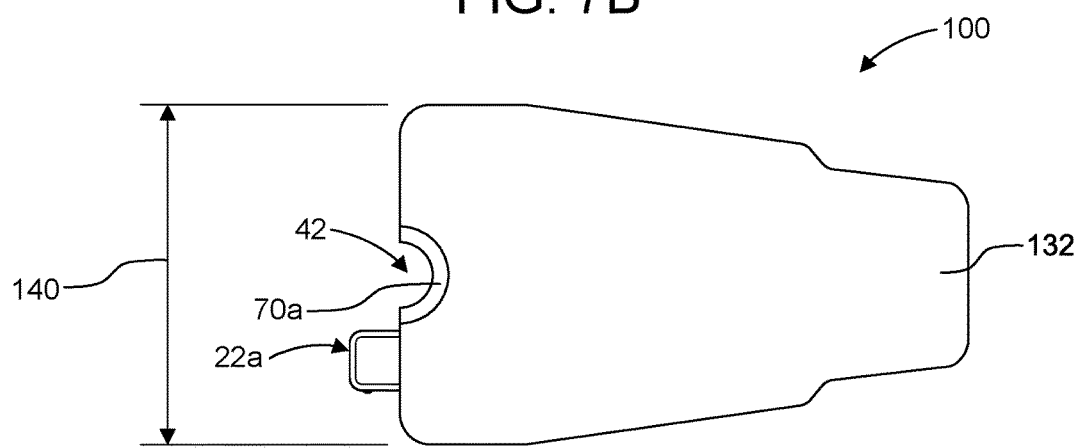

FIGS. 7A-7C depicts various views of member 14a and flexible tab 18a coupled to member 14a (which may together be referred to as a component 100 of stabilizer 10). In the embodiment shown tab 18a is substantially identical to tab 18b. In the embodiment shown, member 14a is configured to be coupled a substantially identical member (e.g., 14b) such that the coupled members (14a and 14b) cooperate to encircle an intraosseous device (e.g., 5) to resist movement of the intraosseous device relative to the members. In some embodiments, member 14a comprises a lower sidewall 104, and one of the one or more flexible tabs (18a) is coupled to lower sidewall 104. For example, in the embodiment shown, tab 18a comprises: a double-sided tape layer 108 having an upper side 112 coupled to a lower surface 116 of lower sidewall 104; and a single-sided tape layer 120 having an adhesive lower side 124 (facing double-sided tape layer 108) coupled to an upper surface 128 of lower sidewall 104 and to a portion of upper side 112 of double-sided tape layer 108 that is not coupled to lower surface 116 of lower sidewall 104. In the embodiment shown, tab 18a also comprises: a liner layer 132 coupled to a lower side (not shown, but facing liner layer 132) of double-sided tape layer 108; and liner layer 132 is configured to be removable from the lower side of double-sided tape layer 108 such that the lower side of the double-sided tape layer can be coupled to skin of a patient. In the embodiment shown, liner layer 132 includes a tab portion 136 that extends beyond at least one peripheral edge of double-sided tape layer 108.

In some embodiments, at least one lateral dimension (e.g., 140 shown in FIG. 7C) of at least one of the flexible tabs (e.g., 18a), when flattened (nor wrinkled, as shown in FIG. 7C), does not exceed 4 inches. For example, in the embodiment shown, lateral dimension 140, when tab 18a is flattened, does not exceed 3.1 inches.

FIGS. 8A-8G depict various views of member 14a that may assist in fully understanding the features of member 14a. In particular, FIG. 8A depicts a top view of member 14a; FIGS. 8B-8C depict front and back side views of member 14a; FIGS. 8D-8F depict left and right side views of member 14a; and FIGS. 8F-8G depicts upper perspective views of member 14a. In the embodiment shown, member 14a is configured such that if two members (e.g., 14a, 14b) are coupled together (as shown in FIGS. 1-2), the two coupled members fit within a rectangular volume no greater than 6 inches cubed. For example, in the embodiment shown, member 14a is configured such that if two members (e.g., 14a, 14b) are coupled together, the two coupled members fit within a rectangular volume no greater than 4 inches cubed. The dimensions shown in FIGS. 8A-8G are accurate for at least one embodiment of members 14a.

Some embodiments of the present kits comprise: three or more of the present members (e.g., 14a) each configured to be coupled to any of the other plurality of members such that the coupled members cooperate to encircle an intraosseous device to resist movement of the intraosseous device relative to the members (e.g., as shown in FIGS. 1-2); and a plurality of flexible tabs (e.g., 18a) each coupled to at least one of the members and comprising an adhesive layer configured to be coupled to skin of a patient.

Some embodiments of the present methods comprise: coupling one of the present apparatuses (e.g., stabilizer 10) to an intraosseous device (e.g., 5) having a portion (e.g., the cannula) extending into a bone of a patient; and coupling the adhesive layer (e.g., bottom side of double-sided tape layer 108) of at least one of the one or more flexible tabs (e.g., 18a) to the patient such that the apparatus (stabilizer) resists motion of the members (e.g., 14a, 14b) relative to the skin to which the adhesive layer (e.g., 108) is coupled. In some embodiments, coupling the apparatus to the intraosseous device is performed while the intraosseous device is coupled to a fluid source (e.g., 78).

Some embodiments of the present methods comprise: coupling a support apparatus (e.g., stabilizer 10) to an intraosseous device (e.g., 5) having a portion (e.g., cannula 66) extending into a bone of patient while the intraosseous device is coupled to a fluid source (e.g., 78); and coupling the support apparatus (e.g., 10) to the skin of patient such that the support apparatus resists displacement of the intraosseous device (e.g., 5) relative to the skin to which the support apparatus is coupled.

The various illustrative embodiments of the present devices and kits are not intended to be limited to the particular forms disclosed. Rather, they include all modifications, equivalents, and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A stabilizer for maintaining an intraosseous device in a stable position, the stabilizer comprising:
   a first stabilizer member having a proximal surface, a distal surface, a first connection portion disposed between the proximal and distal surfaces, and a second connection portion disposed between the proximal and distal surfaces;
   a coupling surface of the first stabilizer member extending from the proximal surface to the distal surface and disposed between the first and second connection portions, the coupling surface defining a portion of a device opening having a longitudinal axis disposed at a non-zero degree angle relative to a plane of the proximal surface of the first stabilizer member;
   a second stabilizer member configured to releasably couple to the first stabilizer member such that the first and second stabilizer members cooperate to resist movement of the intraosseous device;
   the coupling surface of the first stabilizer member defining a first groove and a second groove, the first and second grooves of the first stabilizer member shaped to correspond to a portion of the intraosseous device and configured to receive the portion of the intraosseous device, and
   the portion of the intraosseous device received in the first groove being spaced apart from an insertion site at a position predetermined by a position of the first groove in which the portion of the intraosseous device is received, and
   the portion of the intraosseous device received in the second groove being spaced apart from an insertion site at a position predetermined by a position of the second groove in which the portion of the intraosseous device is received;
   wherein the first and second grooves of the coupling surface are each configured to receive the portion of the intraosseous device in a different position of the intraosseous device relative to the proximal surface of the first stabilizer member.

2. The stabilizer of claim 1, further comprising a first flexible tab coupled to the first stabilizer member, the first flexible tab comprising an adhesive layer configured to be adhered to a patient.

3. The stabilizer of claim 2, further comprising a second flexible tab coupled to the second stabilizer member.

4. The stabilizer of claim 3, wherein the first connection portion of the first stabilizer member is configured as a male connection portion and the second connection portion of the first stabilizer member is configured as a female connection portion.

5. The stabilizer of claim 4, wherein the male connection portion of the first stabilizer member is configured to be inserted into a corresponding female connection portion of the second stabilizer member, and the first female connection portion of the first stabilizer member is configured to receive a corresponding male connection portion of the second stabilizer member.

6. The stabilizer of claim 5, wherein each male connection portion comprises a resilient barb, and each female connection portion comprises a ledge configured such that when the first and second stabilizer members are coupled, the resilient barb of each stabilizer member contacts the ledge of the other stabilizer member to resist separation of the stabilizer members.

7. The stabilizer of claim 6, wherein each barb comprises an arm configured to flex relative to each respective stabilizer member, and a projection configured to move past the ledge of the corresponding female connection portion and mechanically resist separation of the first and second stabilizer members.

8. The stabilizer of claim 3, wherein the second stabilizer member comprises a coupling surface between the two connection portions and configured such that when the two stabilizer members are coupled together, the coupling surfaces cooperate to define the device opening.

9. The stabilizer of claim 8, wherein the longitudinal axis of the device opening is substantially perpendicular to a plane of the proximal surface.

10. The stabilizer of claim 8, wherein the coupling surface of the second stabilizer member defines a first groove and a second groove, the first and second grooves of the second stabilizer member shaped to correspond to a second portion of the intraosseous device and configured to receive the second portion of the intraosseous device.

11. The stabilizer of claim 2, where the first stabilizer member comprises a lower sidewall, and the first flexible tab is coupled to the lower sidewall.

12. The stabilizer of claim 11, wherein the first flexible tab comprises a double-sided tape layer having an upper side coupled to a lower surface of the lower sidewall; and a single-sided tape layer having an adhesive side coupled to an upper surface of the lower sidewall and to a portion of the upper side of the double-sided tape layer that is not coupled to the lower surface of the lower sidewall.

13. The stabilizer of claim 12, wherein the first flexible tab further comprises a liner layer coupled to a lower side of the double-sided tape layer; wherein the liner layer is configured to be removable from the lower side of the double-sided tape layer such that the lower side of the double-sided tape layer can be coupled to skin of a patient; and wherein the liner layer extends beyond at least one peripheral edge of the double-sided tape layer.

14. The stabilizer of claim 1, wherein the first stabilizer member is configured to receive the portion of the intraosseous device in a first position relative to the stabilizer, and further configured to receive the portion of the intraosseous device in a second position relative to the stabilizer.

15. The stabilizer of claim 1, wherein the stabilizer member is formed from a resilient material.

16. The stabilizer of claim 1, wherein the stabilizer member is formed from a partially rigid material.

17. The stabilizer of claim 1, wherein the stabilizer member comprises a substantially rigid portion and a resiliently flexible portion.

18. An apparatus operable to resist displacement of an intraosseous device having a hub, the apparatus comprising:
 a first stabilizer member having a proximal surface, a distal surface, a first connection portion disposed between the proximal and distal surfaces, and a second connection portion disposed between the proximal and distal surfaces;
 a second stabilizer member configured to releasably couple to the first stabilizer member such that the first and second stabilizer members cooperate to resist movement of the intraosseous device; and
 a coupling surface extending from the proximal surface to the distal surface and disposed between the first and second connection portions, the coupling surface defining a portion of a device opening and a pair of grooves,
 a first groove of the pair of grooves configured to receive a flange of the hub of the intraosseous device when the intraosseous device is in a first position relative to the proximal surface, and
 a second groove of the pair of grooves configured to receive the flange of the hub of the intraosseous device when the intraosseous device is in a second position relative to the proximal surface.

19. The stabilizer of claim 18, further comprising a flexible tab coupled to the first stabilizer member, the flexible tab comprising an adhesive layer configured to be adhered to a patient.

20. The stabilizer of claim 18, wherein the first connection portion is a male connection portion and the second connection portion is a female connection portion, the male connection portion comprising a resilient barb, and the female connection portion comprising a ledge, wherein the resilient barb and the ledge are operable to resist separation of the first stabilizer member from the second stabilizer member.

21. An apparatus comprising:
 a stabilizer member having a proximal surface, a distal surface, a first connection portion disposed between the proximal and distal surfaces, and a second connection portion disposed between the proximal and distal surfaces; and
 a coupling surface extending from the proximal surface to the distal surface and disposed between the first and second connection portions, the coupling surface defining a portion of a device opening and a pair of grooves,
 a first groove of the pair of grooves configured to receive a portion of an intraosseous device when the intraosseous device is in a first position relative to the proximal surface, and
 a second groove of the pair of grooves configured to receive the portion of the intraosseous device when the intraosseous device is in a second position relative to the proximal surface,
 wherein the first connection portion is a male connection portion comprising a resilient barb and the second connection portion is a female connection portion comprising a ledge, and
 wherein the resilient barb and the ledge are operable to resist separation of the stabilizer member from another stabilizer member.

* * * * *